United States Patent
Schermeier et al.

(10) Patent No.: US 8,677,994 B2
(45) Date of Patent: Mar. 25, 2014

(54) MULTIPART MEDICAL ENGINEERING SYSTEM

(75) Inventors: Olaf Schermeier, Lübeck (DE); Frank Ziermann, Hamburg (DE)

(73) Assignee: Dräger Medical GmbH, Lübeck (DE)

( * ) Notice: Subject to any disclaimer, the term of this patent is extended or adjusted under 35 U.S.C. 154(b) by 2317 days.

(21) Appl. No.: 11/381,685

(22) Filed: May 4, 2006

(65) Prior Publication Data

US 2006/0278222 A1    Dec. 14, 2006

(30) Foreign Application Priority Data

Jun. 8, 2005  (DE) .......................... 10 2005 026 562

(51) Int. Cl.
*F16K 31/02* (2006.01)
*A61M 16/00* (2006.01)

(52) U.S. Cl.
USPC ................................. 128/204.21; 128/204.18

(58) Field of Classification Search
USPC ............. 128/202.22, 204.18–204.23, 204.29, 128/201.24, 202.27, 203.12–203.18, 128/203.22, 203.25, 203.29, 204.26, 128/206.21, 207.18, 200.24, 203.27, 128/206.29, 207.14; 604/65–67, 533–539, 604/890.1
See application file for complete search history.

(56) References Cited

U.S. PATENT DOCUMENTS

| | | | |
|---|---|---|---|
| 5,400,267 A * | 3/1995 | Denen et al. ..................... | 702/59 |
| 5,910,776 A | 6/1999 | Black | |
| 6,398,727 B1 * | 6/2002 | Bui et al. ...................... | 600/300 |
| 7,151,456 B2 * | 12/2006 | Godfrey ...................... | 340/573.1 |
| 7,338,443 B1 * | 3/2008 | Tucker .......................... | 600/300 |
| 2002/0020414 A1 * | 2/2002 | Fukunaga ................. | 128/205.13 |
| 2002/0038392 A1 | 3/2002 | De La Huerga | |
| 2002/0144682 A1 * | 10/2002 | Kruger et al. ............ | 128/204.18 |
| 2003/0069614 A1 * | 4/2003 | Bowman et al. ................ | 607/60 |
| 2005/0027195 A1 * | 2/2005 | Govari ......................... | 600/433 |
| 2005/0059926 A1 * | 3/2005 | Sage et al. ....................... | 604/65 |
| 2005/0061318 A1 * | 3/2005 | Faram ...................... | 128/204.18 |
| 2005/0133027 A1 * | 6/2005 | Elaz et al. ................ | 128/200.24 |
| 2005/0211761 A1 * | 9/2005 | Anttila et al. ................. | 235/376 |
| 2005/0277911 A1 * | 12/2005 | Stewart et al. ............. | 604/890.1 |

FOREIGN PATENT DOCUMENTS

| | | |
|---|---|---|
| DE | 19625410 A1 | 6/1996 |
| DE | 19809952 A1 | 9/1999 |
| DE | 100 21 783 | 11/2000 |
| DE | 10116650 A1 | 11/2002 |
| EP | 0 571 225 | 11/1993 |
| WO | WO 93/06776 | 4/1993 |
| WO | WO 00/61003 | 10/2000 |
| WO | WO 02/02169 | 1/2002 |
| WO | WO 2004/095379 | 11/2004 |

\* cited by examiner

*Primary Examiner* — Justin R Yu
*Assistant Examiner* — Rachel Young
(74) *Attorney, Agent, or Firm* — McGlew and Tuttle, P.C.

(57) ABSTRACT

A multipart medical engineering system, which comprises at least two components that can be connected via positioning-determining connection feature (410, 411). At least one component (44) is intended to remain in the vicinity of the patient in the connected and unconnected states of the system and at least one component (41) can be removed or replaced with other components in the unconnected state. The component (44) intended to remain in the vicinity of the patient contains a data storage element (45) that can be written to and read via an interface (46) that is mechanically integrated in the position-determining connection means (410, 411).

17 Claims, 4 Drawing Sheets

MULTIPART MEDICAL ENGINEERING SYSTEM

CROSS REFERENCE TO RELATED APPLICATIONS

This application claims the benefit of priority under 35 U.S.C. §119 of German Patent Application DE 10 2005 026 562.6 filed Jun. 8, 2005, the entire contents of which are incorporated herein by reference.

FIELD OF THE INVENTION

The present invention pertains to a multipart medical engineering system with a multifunctional interface.

BACKGROUND OF THE INVENTION

Medical engineering systems are characterized by increasing complexity and modularity. As a rule, a plurality of components are to be connected before a medical engineering system is ready to use at all. Numerous interfaces are usually to be connected to a connection means or connection device, which may require a great effort, imply a high risk for errors and possibly availability problems.

Besides connections that are necessary to embody different material flows, possibilities of establishing data connections are of increasing significance. Numerous data must be kept permanently available during medical treatments. At the same time, a large amount of other data, which must be logged and/or taken into account in therapeutic decisions, is generated during the treatment of patients. Loss of such data, which can definitely happen under the time pressure that usually prevails, requires increased effort for restoring the data or for further data acquisition. Numerous data interfaces are known, which are connected to separate cables or other connection means in order to allow medical engineering components to communicate with one another.

Furthermore, it is known that external data storage media with data sets can be kept ready in order to make it possible to perform the expedited adaptation of medical engineering components when needed. It is known, for example, that certain modes of operation or control modes can be released or blocked on medical engineering devices by means of external data storage media (DE 101 16 650 A1).

Furthermore, it is known that such units can be adapted to the needs of individual operators by external data storage media and the connection thereof with complex, computer-controlled medical engineering units (DE 196 25 410 A1).

Finally, it is known that sets of settings and parameters of medical engineering devices, for example, of an ECG (Electrocardiogram) monitor, which are generated during a treatment, can be stored in an external memory and that this memory can be read by the new device after the particular device is replaced with a new device. It thus becomes unnecessary to manually transfer sets of parameters or settings (DE 198 09 952 A1).

It is common to the above examples of the state of the art that an external memory, which is configured especially for storing and making available special data sets, must always be connected to a medical engineering device in order to completely establish the ability to function. This requires, on the one hand, special actions and requires increased attention because such data storage media, usually designed as a chip card, may be lost in a short time in work processes taking place under a high time pressure, which would lead to a considerable stagnation or a subsequent effort.

SUMMARY OF THE INVENTION

The object of the present invention is to provide the possibility of reducing the risk for operating errors or data loss in complex medical systems without the need for substantially increased efforts.

According to the invention, a multipart medical engineering system is provided which comprises at least two components connected via a position-determining connection means. At least one of the components is intended to remain in the vicinity of the patient in the connected and unconnected states of the system. At least one component can be removed or replaced with other components in the unconnected state. The component intended to remain in the vicinity of the patient contains a data storage means which can be written to and read from via an interface. The interface is mechanically integrated in the position-determining connection means.

The present invention is based essentially on two principles. The first principle is that numerous multipart medical engineering systems have connection elements by means of which individual components are connected to one another. In many cases, these connection elements require accurate positioning in order to perform a connection.

Fluidic interfaces, in particular, often have suitable connection means, which are connected to one another, in order to embody structure for an exchange of substances. The frequent requirement that such fluidic interfaces be sealed requires that these be positioned very accurately for a correct connection. Alternatively they may be designed by means of a corresponding guide means such that incorrect positioning is extensively ruled out.

Another principle is that components that are intended to be left in the vicinity of a patient for a rather long time are frequently present in modern medical engineering systems, while other components are replaced more frequently or are connected to the patient or the medical engineering system for a short time only. If a data storage means is connected to such a component, which remains in the vicinity of a patient for a longer time, loss of this data storage medium is nearly ruled out while it remains in the vicinity of the patient. If, furthermore, the component that remains in the vicinity of the patient for a longer time is equipped for this purpose with a data storage medium that can be actuated via an interface that is mechanically integrated in the already actuated connection means, it is guaranteed, furthermore, that the data storage medium is available, on the one hand, in case of the connected components and that, on the other hand, the interface for actuating the data storage medium is positioned accurately in respect to other components that are connected to the component that remains in the vicinity of the patient. Especially accurate positioning is obtained, if the interface for actuating the data storage medium is mechanically integrated in a fluidic interface, via which the component remaining in the vicinity of the patient is connected to other components of the multipart medical engineering system.

The present invention consists of a multipart medical engineering system, which comprises at least two components that can be connected via position-determining connection means, wherein at least one of the components is intended to remain in the vicinity of the patient in the connected state and in the unconnected state of the system and at least one component can be removed or replaced with other components in the unconnected state, wherein the component intended to remain in the vicinity of the patient contains data storage means, which can be written to and read via an interface, which is mechanically integrated in the position-determining connection means. Position-determining connection means are defined here as means that must assume a defined position in relation to one another in order to make it possible to establish the desired connection.

The interface for actuating the data storage means, which is present according to the present invention, is advantageously integrated in a fluidic interface. A fluidic interface in the sense of the present invention is defined as any connection system that can interact with one another via complementary shaped parts, while a sealing action is achieved in a positive-locking or nonpositive manner and exchange of a fluid can take place through the connected interface in the connected state. Typical fluids are breathing gases and liquids during intensive care procedures.

The connection means that can be connected to one another and the parts of the fluidic interface that can be connected to one another are connected to data transmission means in an at least sufficiently dimensionally stable manner in such a manner that ensures that in the case of the components of the medical engineering system according to the present invention that are connected to one another, the data transmission means, which form the interface for actuating the data storage medium, are arranged at least such that data transmission can take place. This principle of integrating data transmission means in parts of a fluidic interface that can be connected to one another or in other, position-determining connection means that can be connected to one another is defined as integration in the sense of the present invention.

The connection of a data storage means with a component that remains in the vicinity of a patient for a longer time is automatically linked with the fact that no additional actions are necessary for readying the memory and the memory can never be forgotten. Due to the integration of the data transmission means in an interface, which must be connected to complementary parts anyway for the operation of the medical engineering system, it is achieved, furthermore, that no additional actions are necessary for contacting the data storage means with a writing or reading unit, which is located in another component of the medical engineering system, which is highly advantageous for a process taking place under time pressure.

The components that are intended to remain in the vicinity of a patient for a longer time are especially breathing tube systems. These breathing tube systems are equipped according to the present invention with data storage means. Components of a medical engineering system according to the present invention that can be removed from the patient or replaced regularly may be, for example, respirators.

As an alternative, other components, which remain in the vicinity of a patient for a longer time, may be equipped with data storage means according to the present invention. These components may contain especially at least one tube, a mask body, a filter, an $SPO_2$ sensor, ECG electrode sets or body temperature sensors or catheters. All these components are usually designed such that they can be connected to other components of medical engineering systems without problems via interfaces, at times even fluidic interfaces.

It is especially advantageous if the interface according to the present invention is equipped with means for contactless data transmission, which is especially advantageous in case of handling oxygen.

It is undoubtedly advantageous if the data storage means and/or data transmission means are designed such that they are suitable for the storage and the transmission of respiration parameters, which makes possible the comfortable replacement of the devices especially in case of the use of changing respirators during the treatment of a patient.

In an advantageous embodiment of a system according to the present invention, the data storage means and/or data transmission means are designed such that they are suitable for the storage and transmission of data on the components connected by means of the interface. This is an advantageous variant especially in the case of the use of breathing tube systems that can be easily confused with one another. This system can automatically recognize the type of tube connected in this case.

In more comfortable, multipart medical engineering systems with an interface according to the present invention, the data storage means and/or data transmission means are designed such that they are suitable for the storage and the transmission of patient data, therapy data and/or diagnostic data. The data storage means can thus sometimes assume the function of an electronic patient file and make necessary data automatically available to the attending physician.

It proved to be especially advantageous if the data transmission means and/or data storage means are parts of an RFID system.

As an alternative, the data transmission means and/or data storage means may be parts of a system that is based on magnetic or optical data storage and/or data transmission. The one-wire technology represents another advantageous alternative.

To prevent unauthorized access to the data being stored, it is advantageous to code the data and to make them available only by a corresponding decoding method. It is necessary for this that means for coding and decoding the transmitted and/or stored data be contained.

Furthermore, it is advantageous if means are contained that make it possible to manually store information that prohibits the further use of the component intended to remain at the patient. These include, for example, a manual switch, which ensures the transmission and the storage of a blocking code on actuation. If this code is subsequently read, the medical engineering system requires the replacement of the component being blocked. This may be useful in case of unclear risks for infection or obvious damage.

The present invention will be explained in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
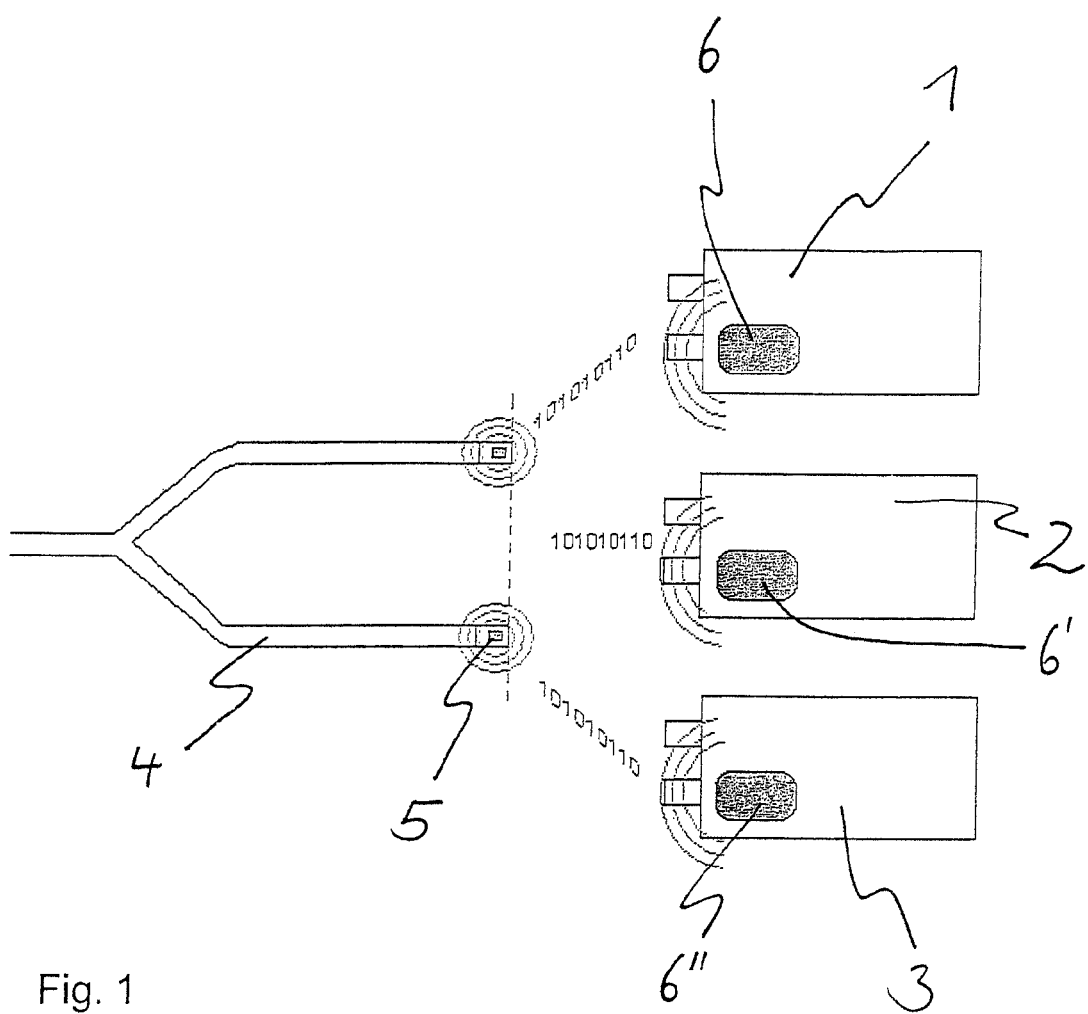
FIG. 1 is a schematic view of a multipart medical engineering system according to the present invention in the form of a respiration system.

Referring to the drawings in particular, a respiration system equipped according to the present invention comprises a breathing tube system with a memory element as the component that is intended to remain in the vicinity of a patient for a longer time in the sense of the present invention. Respirators, which have a reading and writing unit, which can communicate with the memory element when the breathing tube system is connected, are comprised as components that can be regularly removed from the patient or replaced. This offers numerous advantages over conventional respiration systems, as they will be described below.

There are a large number of different types of breathing tubes. Thus, there are disposable tubes and tubes that can be used several times, different tube lengths, different diameters, double tube systems, coaxial tubes, tubes with a semipermeable membrane for the passage of moisture, tubes heated by electric heating wires, and tubes with temperature sensors and flow meters.

Many patients are respirated mechanically within the framework of their medical care, and different respiration systems may be used now one after another in the course of the treatment.

Any combination of a certain type of tube with a certain respirator requires certain respiration parameters and rules out other respiration parameters. In addition, respiration parameters must be selected according to therapeutic criteria. The essential parameters are the form of respiration, the oxygen content, the respiration rate, optionally the stroke volume, the maximum volume, the respiration pressure and a maximum allowable pressure.

Currently existing respiration systems make it necessary for the individual respiration parameters of a particular patient to be set manually by the user at the device in order to ensure optimal treatment.

The optimal setting of the parameters depends on a large number of individual factors of the patient, which describe the respiration demand. The optimal setting of the respiration parameters therefore requires a considerable amount of time on the part of the operating staff.

After the beginning of the medical care, a patient usually passes through different stations. These may be an ambulance/helicopter, outpatient department, induction, OP, termination, intensive care unit and various transportations inside and outside the hospital. If respiration is required for a patient, the parameters must be set anew by the personnel for each respiration system along this chain in conventional systems.

The effort described decreases and the risk for error is substantially diminished due to the use of a respiration system equipped according to the present invention. Respiration parameters can be stored as a data set in the memory element, which is integrated in the breathing tube system. The breathing tube system remains at the patient in case of a change of the clinical area or the respirator. After another respirator is connected, these data are available to the newly connected respirator, which makes possible the automatic or semi-automatic setting of the necessary respiration parameters. Furthermore, data on forbidden parameters, which must not be set by any means when the particular type of tube is used, can be stored, which markedly reduces the risk for the incorrect treatment of the patients. In addition or as an alternative to respiration parameters, data on a performed treatment can be stored in the memory element and read later for accounting purposes. For example, it is thus possible to log the minutes of respiration performed.

FIG. 1 shows a multipart medical engineering system according to the present invention in the form of a respirator. The exemplary embodiment pertains to a system comprising at least two respirators, three respirators 1, 2, 3 here, and at least one breathing tube system 4, wherein the respirators are capable of storing and reading individual respiration parameters of the patient on a memory element 5 on the breathing tube system 4 in a contactless manner when one of the respirators 1, 2, 3 is connected to the breathing tube system 4. The respirators are an emergency respirator 1, an intensive care respirator 2 and an anesthesia respirator 3, as they may be used at a patient at different points in time.

The connection is established such that respiration parameters of one respirator are stored with a respective writing and reading unit 6, 6', 6" on the memory element 5 of the breathing tube system 4 and these parameters are read by the other respirators from the memory element 5 in the breathing tube system 4 and can thus be set automatically or semi-automatically by the individual respirators. It is thus achieved that the respiration parameters set on the first respirator are also set on the other respirator after the breathing tube system is plugged into that other respirator.

Basic requirements on breathing tubes are described in EN 12342. This standard also defines the mechanical interfaces to the respiration system, which are usually designed with a conical male connector at the respiration system and a female connector at the breathing tube. The common standards of 22 mm, 15 mm and 10 mm diameter exist for the connectors. This connector system is a fluidic interface in the sense of the present invention, which ensures the accurate positioning of the shaped parts that are in contact with one another in the connected state.

Each respirator automatically stores all settings of the respiration parameters in the memory element in the breathing tube system. After the tube is plugged into another respiration system, the latter automatically reads the data last stored in the memory element and sets these on the new respiration system. This may optionally happen after polling and confirmation on the display screen. If any change is made again in the settings in this system, this is automatically stored in the memory element and is optionally transmitted to another respiration system. In order not to change the process within the clinical procedure, a passive, cableless memory element is used, which can be read without additional working steps.

The advantage of the solution for the user is the marked simplification of the clinical processes and consequently a reduction of the costs due to fewer and shorter working steps.

The complicated manual individual programming of every individual respirator for a particular patient is eliminated and is replaced by a brief polling. After a change in the clinical area or the respiration system, the setting of optimal respiration parameters can be carried out in a few seconds, whereas substantially more time is needed for this in conventional systems. Furthermore, optimal treatment of the patient is ensured in all areas because errors in operating the system are extensively ruled out. Due to the continued use of optimized respiration parameters on different devices, a stable and lastingly optimized state of respiration can be achieved.

The communication between the breathing tube system and the particular respirator takes place via a contactless data connection in the exemplary embodiment.

The memory element is embodied by an RFID chip, a so-called tag, in the tube nozzle. This tag is applied either by bonding or injection. It is arranged geometrically in the tube nozzle such that it can be read and written to by a writing and reading unit in the respirator via an antenna when the breathing tube system is connected to the respirator.

The RFID embodies an inductive method, in which an antenna on a tag is excited with a defined frequency. A small chip on the RFID tag thereupon sends back the stored data. There are a large number of different RFID standards and RFID tags with different functionalities.

Figure 2:
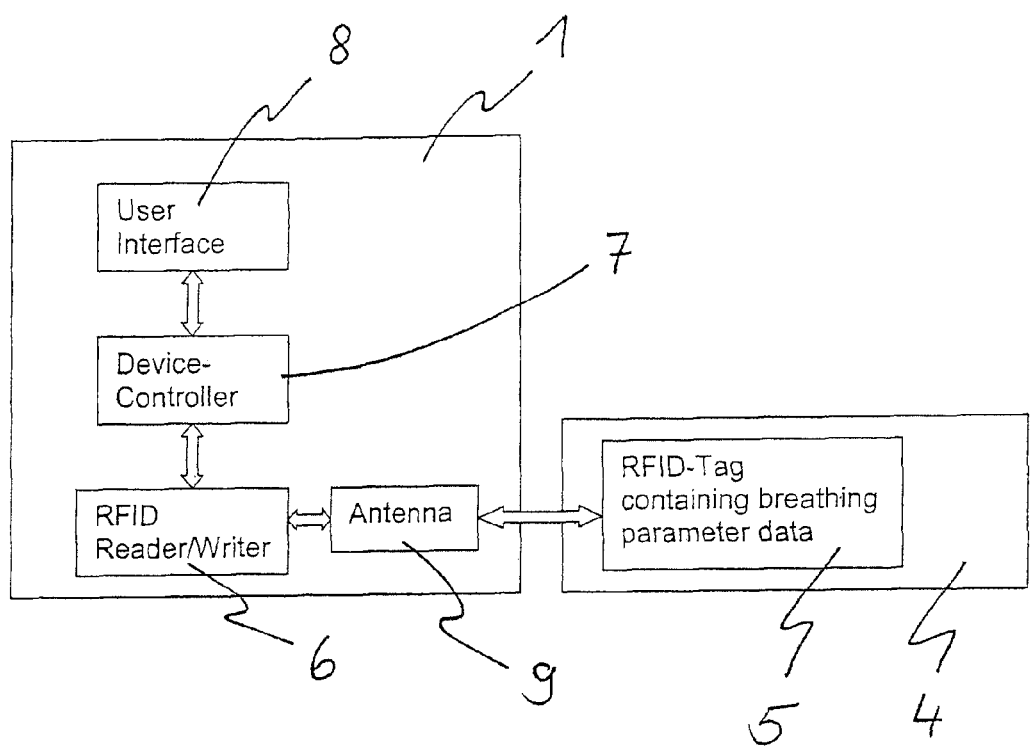
FIG. 2 is a block diagram of a multipart medical engineering system according to the present invention.

FIG. 2 shows a block diagram of a multipart medical engineering system according to the present invention in the form of a respiration system. The respirator 1 itself contains a control unit 7, which controls all the processes taking place during the operation of the device. Data necessary for this can be entered via an operating unit 8. The breathing tube system 4, which can be connected to the respirator 1, has an RFID tag as a memory element 5. A writing and reading unit 6 in the respirator 1 can communicate with this RFID tag, which is embodied via a corresponding antenna 9. The writing and reading unit 6 van likewise pass on the data read from the RFID tag to the control unit 7. If the RFID tag contains data on respiration parameters, these may replace an entry via the operating unit. The respiration parameters read can be displayed, instead, on the operating unit 8 and taken over by the user as a setting by a release.

Various data are already written to the RFID tag in the state in which the breathing tube system is supplied. These contain data in the form of an identification number, a manufacturer code, and make possible the reading of the date of manufacture and other specific data. Furthermore, respiration parameters, which must not be set with the respiration system, are stored. For example, it can thus be prevented that large stroke volumes, which would be typical of the respiration of adult patients, be set on the respirator when a breathing tube system is used for newborns.

When the respirator recognizes the RFID tag, this means that a tube is connected. Respiration parameters that may already have been stored on the RFID tag are then regularly compared with the respiration parameters set with the software of the device and stored on the RFID tag in case of a change by the user. Conversely, after the breathing tube system has been connected to a respirator, the stored respiration parameters are read from the RFID tag by means of the writing and reading unit and used, after release, automatically or semi-automatically for setting the mode of respiration, which is usually performed by the software of the device.

Figure 3:
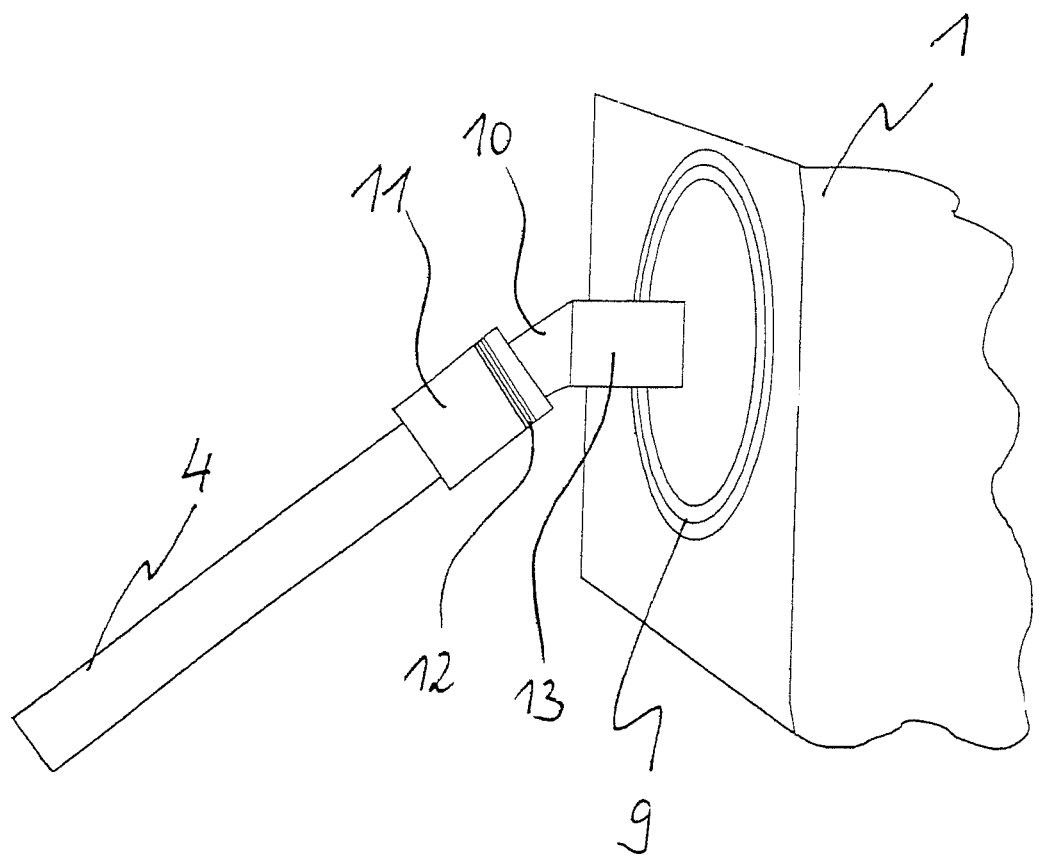
FIG. 3 is a respiration system according to the present invention in the area of a fluidic interface.

FIG. 3 shows a respiration system according to the present invention in the area of the fluidic interface. A breathing gas connection with a variable-angle male connector 10 is arranged at a respirator 1. A breathing tube system 4 is connected at this connector 10 by connecting a sealing nozzle 11 as a female connector with the male connector 10. An RFID tag, not visible in this figure, is connected to an antenna 12. In this example, a coil is injected as an antenna 12 of the tag into the nozzle 11 such that its windings are directed at right angles to the axis of the tube connection. An antenna 9 of a device-side writing and reading unit is arranged in this variant at right angles to the axis of the part of the breathing gas connection 13, which said part is rigidly connected to the respirator 1. It is thus achieved that all fields that are formed around the antennas 9, 12 have a parallel component in relation to the receiving antenna in all positions of the variable-angle male connector 10 (except in the case of a connector bent at right angles), which ensures an inductive coupling sufficient for carrying out the present invention.

Figure 4:
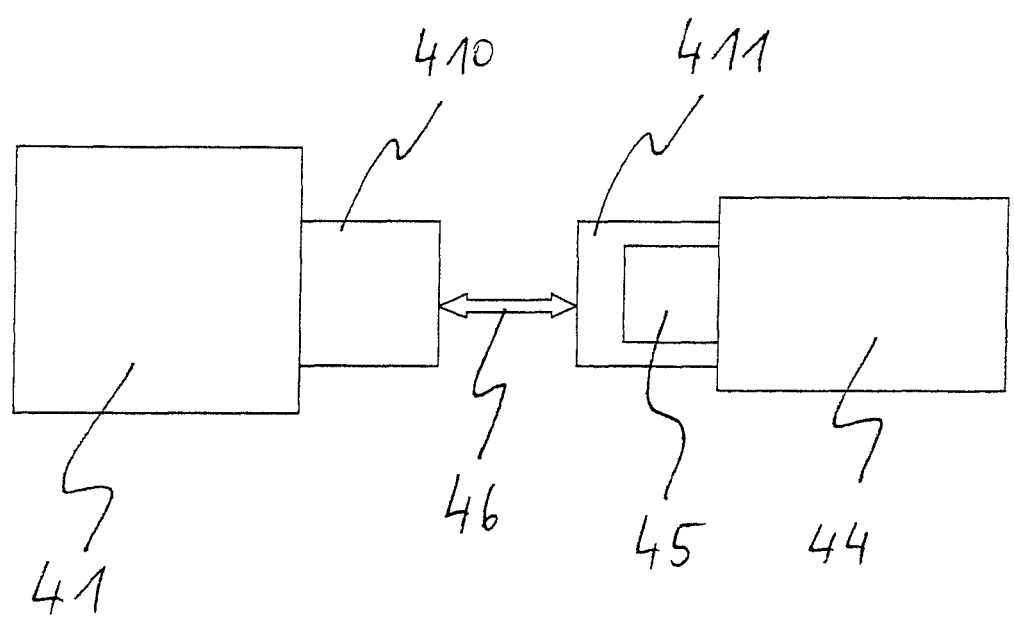
FIG. 4 is a schematic view showing the general design of a multipart medical engineering system according to the present invention.

FIG. 4 shows once again the general design of a multipart medical engineering system according to the present invention. It is a multipart medical engineering system which comprises at least two components that can be connected via position-determining connection means 410, 411, wherein at least one component 44 is intended to remain in the vicinity of the patient in the connected and unconnected states of the system and at least one component 41 can be removed and replaced with other components in the unconnected state, the component 44 intended to remain in the vicinity of the patient containing data storage means 45, which can be written to and read via an interface 46, which is mechanically integrated in the position-determining connection means 410, 411.

While specific embodiments of the invention have been shown and described in detail to illustrate the application of the principles of the invention, it will be understood that the invention may be embodied otherwise without departing from such principles.

What is claimed is:

1. A multipart medical engineering system comprising:
   a data read/write interface;
   a position-determining connection;
   two components that can be connected via said position-determining connection, at least one of said components remaining in a vicinity of a patient in a connected state and in an unconnected state of the system and at least one of said components being removed or replaced with other components in the unconnected state, said position-determining connection including a connection part of said component remaining in the vicinity of the patient in said connected state and in said unconnected state of the system and a connection part of said component being removed or replaced, said data read/write interface being mechanically integrated adjacent to or in said connection part of said components being removed or replaced; and
   a data storage means, said data storage means being mechanically integrated in said connection part of said component remaining in the vicinity of the patient in said connected state and in said unconnected state of the system or mechanically integrated in said component intended to remain in the vicinity of the patient in said connected state and in said unconnected state of the system, said data storage means being written to and read from via said interface, said data storage means comprising respiration parameter data, wherein said component intended to remain at the patient includes a breathing tube system.

2. A multipart medical engineering system in accordance with claim 1, wherein said position-determining connection is part of a fluidic interface and said two components are fluidicly connected therewith, said connection part of said component intended to remain in the vicinity of the patient being arranged at a position external to the patient, said data storage means being located at a spaced location from said connection part of said component being removed or replaced in said unconnected state of the system.

3. A multipart medical engineering system in accordance with claim 1, wherein said component that can be removed from the patient is a respirator.

4. A multipart medical engineering system in accordance with claim 1, wherein said data read/write interface includes means for contactless data transmission.

5. A multipart medical engineering system in accordance with claim 1, wherein at least one of said data storage means and said data transmission means are designed such that they are suitable for the storage and the transmission of at least one of patient data, accounting data, therapy data and diagnostic data.

6. A multipart medical engineering system in accordance with claim 1, wherein said data read/write interface includes a data transmission means and at least one of said data storage means and said data transmission means store and transmit respiration parameters.

7. A multipart medical engineering system in accordance with claim 1, wherein said data read/write interface includes a data transmission means and at least one of said data storage means and data transmission means store and transmit data on the components connected by means of the interface.

8. A multipart medical engineering system in accordance with claim 1, wherein said data read/write interface includes a data transmission means and at least one of said data storage means and data transmission means comprise a RFID system.

9. A multipart medical engineering system in accordance with claim 1, wherein said data read/write interface includes a data transmission means and at least one of said data storage means and data transmission means are part of a one-wire system.

10. A multipart medical engineering system in accordance with claim 1, wherein said data read/write interface includes a data transmission means and at least one of said data storage means and data transmission means are suitable for one or more of optical data transmission and data storage.

11. A multipart medical engineering system in accordance with claim 1, wherein said data read/write interface includes a data transmission means and at least one of said data storage means and data transmission means comprise at least one magnetic storage medium.

12. A multipart medical engineering system in accordance with claim 1, wherein said data read/write interface includes means for coding and decoding at least one of the transmitted and stored data.

13. A multipart medical engineering system in accordance with claim 1, further comprising blocking means to manually store information that prohibits the further use of the component intended to remain at the patient.

14. A multipart medical engineering system comprising:
a patient locale component remaining in a vicinity of a patient in both a system connected state and a system unconnected state;
a removable/replaceable component that can be removed or replaced with other components in the system unconnected state;
a position-determining connection providing an operative fluidic connection between said patient locale component and said removable/replaceable component to allow fluid to pass between said patient locale component and said removable/replaceable component and for fixing a region of operation of said patient locale component relative to said removable/replaceable component based on said operative fluidic connection between said patient locale component and said removable/replaceable component, said position-determining connection including a connection part connected to said patient locale component and a connection part connected to said removable/replaceable component, said connection part connected to said patient locale component remaining in the vicinity of patient in said system connected state and said system unconnected state;
a data storage element operatively connected to said connection part connected to said patient locale component, said data storage element comprising patient respiration parameter data; and
a data read/write interface that is mechanically integrated in the removable/replaceable component, said data read/write interface for reading data from said data storage element when said patient locale component is connected to said removable/replaceable component by said position-determining connection, wherein said removable/replaceable component is a respirator and said patient locale component is a breathing tube or one or more components of a breathing tube system.

15. A multipart medical engineering system in accordance with claim 14, wherein said data read/write interface includes a means for contactless data transmission, said connection part connected to said patient locale component being arranged in the vicinity of the patient at a position external to the patient, said connection part connected to said patient locale component being located at a spaced location from said connection part connected to said removable/replaceable component in said system unconnected state.

16. A multipart medical respiration system comprising:
a patient breathing tube system component remaining connected to or in a vicinity of a patient in both a system connected state and a system unconnected state;
a plurality of respirators, each respirator being connectable to the patient breathing tube system component to provide at least one connected respirator, connected to the patient breathing tube system component in the system connected state and each respirator being a removable/replaceable component that can be removed or replaced with at least one other of said plurality of respirators in the system unconnected state;
a position-determining connection providing an operative connection between said patient breathing tube system component and said at least one connected respirator component, said position-determining connection including a patient breathing tube system component connection part connected to said patient breathing tube system component and including a respirator connection part, with each of said plurality of respirators including a respirator connection part, said position-determining connection fixing a position of said breathing tube system component connection part relative to said respirator connection part of said at least one connected respirator in a system connected state;
a data storage element connected to said breathing tube system component connection part, said data storage element being connected to or in the vicinity of the patient in said system connected state and said system unconnected state; and
a data read/write interface that is mechanically integrated in each of said plurality of respirators, said data read/write interface for reading data from said data storage element when said patient breathing tube system component is connected to said at least one connected respirator in a system connected state with said position-determining connection establishing a data read/write data transfer location between said data storage element and said data read/write interface.

17. A multipart medical engineering system in accordance with claim 16, wherein said patient breathing tube system component connection part is arranged at a position external to the patient, said patient breathing tube system component connection part being located at a spaced location from at least one of said respirators in said system unconnected state.

* * * * *